US010172511B2

(12) United States Patent
Hiraoka

(10) Patent No.: US 10,172,511 B2
(45) Date of Patent: Jan. 8, 2019

(54) ENDOSCOPE

(71) Applicant: OLYMPUS CORPORATION, Tokyo (JP)

(72) Inventor: Jin Hiraoka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/614,865

(22) Filed: Jun. 6, 2017

(65) Prior Publication Data
US 2017/0265718 A1    Sep. 21, 2017

Related U.S. Application Data

(63) Continuation of application No. PCT/JP2016/068008, filed on Jun. 16, 2016.

(30) Foreign Application Priority Data

Jun. 18, 2015    (JP) ................. 2015-123095

(51) Int. Cl.
*A61B 1/00*    (2006.01)
*A61B 1/005*    (2006.01)
(Continued)

(52) U.S. Cl.
CPC ........ *A61B 1/0051* (2013.01); *A61B 1/00011* (2013.01); *A61B 1/00098* (2013.01);
(Continued)

(58) Field of Classification Search
CPC .............. A61B 1/00098; A61B 1/0051; A61B 1/00011; A61B 1/06; A61B 1/012; A61B 1/00009; A61B 1/00165
See application file for complete search history.

(56) References Cited

U.S. PATENT DOCUMENTS 4,653,476 A * 3/1987 Bonnet .............. A61B 1/00098
600/106
5,343,853 A * 9/1994 Komi ................. A61B 1/00098
600/107

(Continued)

FOREIGN PATENT DOCUMENTS

JP    H05-123288 A    5/1993
JP    H07-184831 A    7/1995

(Continued)

OTHER PUBLICATIONS

International Search Report dated Aug. 23, 2016 issued in PCT/JP2016/068008.

*Primary Examiner* — Timothy J Neal
(74) *Attorney, Agent, or Firm* — Scully, Scott, Murphy & Presser, P.C.

(57) ABSTRACT

An endoscope includes: an insertion section inserted into a subject; an operating unit continuously connected to a proximal end of the insertion section; an observation unit disposed at a distal end of the insertion section, and configured to observe the subject; a treatment instrument insertion passage configured to allow insertion of a treatment instrument providing medical treatment to the subject, and project the treatment instrument from a distal end portion of the insertion section; a distal bending portion disposed at a distal end of the treatment instrument insertion passage, and configured to bend according to a raising operation of the operating unit, the distal bending portion including a tube including a super elastic alloy and including a slit formed to reduce power required for the bending operation, and being configured to raise the treatment instrument; and a coating portion provided to cover the distal bending portion.

18 Claims, 12 Drawing Sheets

(51) Int. Cl.
    *A61B 8/12*     (2006.01)
    *A61B 1/018*     (2006.01)
    *G02B 23/24*     (2006.01)
    *A61B 1/012*     (2006.01)
    *A61B 1/06*     (2006.01)
    *G02B 23/26*     (2006.01)

(52) U.S. Cl.
    CPC ................ *A61B 1/018* (2013.01); *A61B 8/12* (2013.01); *G02B 23/2476* (2013.01); *A61B 1/0008* (2013.01); *A61B 1/00009* (2013.01); *A61B 1/0057* (2013.01); *A61B 1/00064* (2013.01); *A61B 1/00165* (2013.01); *A61B 1/012* (2013.01); *A61B 1/06* (2013.01); *G02B 23/26* (2013.01)

(56) References Cited

U.S. PATENT DOCUMENTS

| | | | |
|---|---|---|---|
| 5,460,168 A * | 10/1995 | Masubuchi | A61B 1/00096 600/107 |
| 9,125,551 B2 | 9/2015 | Muyari et al. | |
| 2007/0197871 A1 * | 8/2007 | Geitz | A61B 1/00098 600/117 |
| 2008/0177135 A1 | 7/2008 | Muyari et al. | |
| 2011/0112365 A1 * | 5/2011 | Galperin | A61B 1/00066 600/118 |

FOREIGN PATENT DOCUMENTS

| JP | H08-215140 A | 8/1996 |
|---|---|---|
| JP | 2000-116598 A | 4/2000 |
| JP | 2008-173369 A | 7/2008 |

* cited by examiner

ENDOSCOPE

CROSS-REFERENCE TO RELATED APPLICATIONS

This application is a continuation of PCT international application Ser. No. PCT/JP2016/068008 filed on Jun. 16, 2016 which designates the United States, incorporated herein by reference, and which claims the benefit of priority from Japanese Patent Applications No. 2015-123095, filed on Jun. 18, 2015, incorporated herein by reference.

BACKGROUND

The present disclosure relates to an endoscope.

Endoscopes are known that are inserted into subjects' bodies to perform observation or the like of regions to be examined, and the endoscopes are widely used in medical field and the like. In recent years, some endoscopes include treatment instrument raisers which deliver to affected areas treatment instruments, such as puncture needles, for treatment in subjects. For example, in JP 2000-116598 A, an endoscope is disclosed which includes a treatment instrument raiser having a multi-joint structure obtained by turnably connecting flat plate members in sequence, and a wire for raising operation, connected to a distal end of the treatment instrument raiser. In this endoscope, when a user, such as a physician, performs raising operation to pull the wire toward a proximal end, flat plate members of the treatment instrument raiser are sequentially turned, and a treatment instrument is raised.

There is a need for an endoscope which has improved cleaning efficiency.

SUMMARY

An endoscope according to one aspect of the present disclosure includes: an insertion section inserted into a subject; an operating unit continuously connected to a proximal end of the insertion section; an observation unit disposed at a distal end of the insertion section, and configured to observe the subject; a treatment instrument insertion passage configured to allow insertion of a treatment instrument providing medical treatment to the subject, and project the treatment instrument from a distal end portion of the insertion section; a distal bending portion disposed at a distal end of the treatment instrument insertion passage, and configured to bend according to a raising operation of the operating unit, the distal bending portion including a tube including a super elastic alloy and including a slit formed to reduce power required for the bending operation, and the distal bending portion being configured to raise the treatment instrument; and a coating portion provided to cover the distal bending portion.

An endoscope according to another aspect of the present disclosure includes: an insertion section inserted into a subject; an operating unit continuously connected to a proximal end of the insertion section; an observation unit disposed at a distal end of the insertion section, and configured to observe the subject; a treatment instrument insertion passage configured to allow insertion of a treatment instrument providing medical treatment to the subject, and project the treatment instrument from a distal end portion of the insertion section; a distal bending portion disposed at a distal end of the treatment instrument insertion passage, the distal bending portion having an oval cross-section orthogonal to a direction in which the insertion section extends, and the distal bending portion being configured to bend according to a raising operation of the operating unit and raise the treatment instrument; and a coating portion provided to cover the distal bending portion.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

Figure 1:
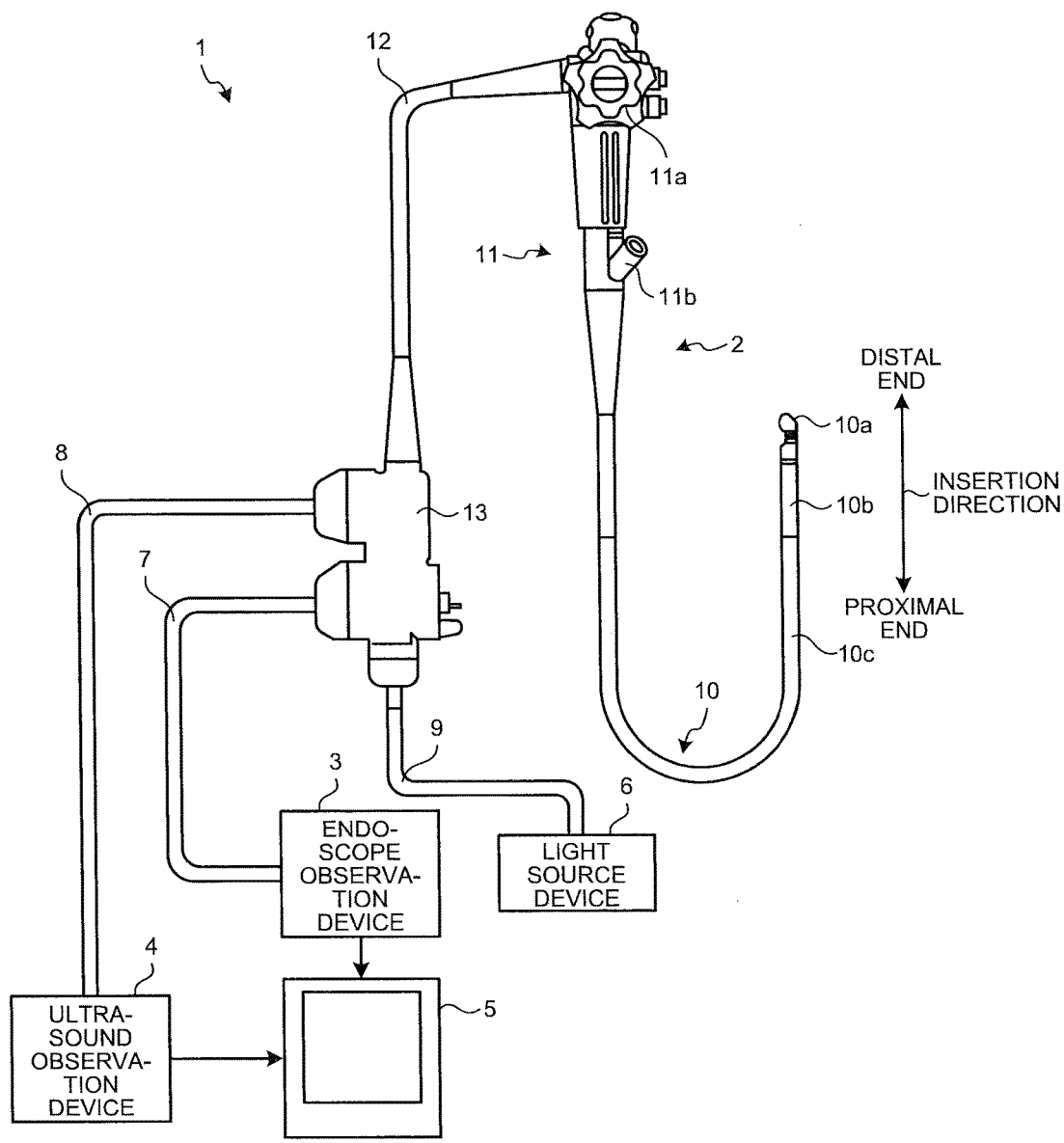
FIG. 1 is a schematic view illustrating a configuration of an ultrasound diagnostic system including an ultrasound endoscope according to a first embodiment of the present disclosure.

Embodiments of an endoscope according to the present disclosure will be described below with reference to the drawings. Note that, the present disclosure is not limited to these embodiments. In the following embodiments, an ultrasound endoscope including an ultrasound transducer for ultrasound observation of an object to be observed is described as an example, but the present disclosure may be applied to general endoscopes using treatment instruments such as puncture needles for treatment in subjects.

Furthermore, in the drawings, the same or corresponding elements are appropriately denoted by the same reference signs. Furthermore, the drawings are schematically illustrated, and dimensional relationships, ratios, or the like between the elements may be different from those of actual one. In addition, the drawings may include portions having different positional relationships or ratios.

First Embodiment

FIG. 1 is a schematic view illustrating a configuration of an ultrasound diagnostic system including an ultrasound endoscope according to a first embodiment of the present disclosure. An ultrasound diagnostic system 1 illustrated in FIG. 1 includes an ultrasound endoscope 2, an endoscope observation device 3, an ultrasound observation device 4, a display device 5, a light source device 6, a video cable 7 connecting the ultrasound endoscope 2 and the endoscope observation device 3, an ultrasound cable 8 connecting the ultrasound endoscope 2 and the ultrasound observation device 4, and a light source cable 9 connecting the ultrasound endoscope 2 and the light source device 6.

The ultrasound endoscope 2 is an endoscope which includes, as an observation unit observing an object to be observed, an imaging unit including an optical system focusing light reflected from the object to be observed, and an imaging element converting the focused light to an electrical signal, and outputting the electrical signal and an ultrasound transducer unit receiving an ultrasound wave reflected from an object to be observed to output an electrical signal. The endoscope observation device 3 controls an endoscopic observation function, and processes an output signal output from the ultrasound endoscope 2 during endoscopic observation. The ultrasound observation device 4 controls an ultrasound observation function, and processes an output signal output from the ultrasound endoscope 2 during ultrasound observation. The display device 5 for example acquires signals output from the endoscope observation device 3 and the ultrasound observation device 4, and appropriately displays at least one of an endoscopic image and an ultrasound tomographic image. The light source device 6 includes a light source for supplying illumination light for endoscopic observation.

The ultrasound endoscope 2 includes an insertion section 10 having a distal end disposed with the observation unit, and inserted into a subject, an operating unit 11 continuously connected to a proximal end of the insertion section 10, a universal cord 12 extending from a side portion of the operating unit 11, and a connector portion 13 continuously connected to the universal cord 12, and connected to the video cable 7, the ultrasound cable 8, and the light source cable 9. Note that, in the present description, as illustrated in FIG. 1, a direction in which the insertion section 10 is inserted is defined as "insertion direction", and in the following description, "distal end" represents a leading end in the insertion direction, and "proximal end" represents an opposite end (near the operating unit 11) to the leading end in the insertion direction.

The insertion section 10 includes, sequentially from the distal end, a distal end portion 10a, a bending section 10b configured to be bent according to rotation operation of a bending knob 11a provided at the operating unit 11, and a flexible tube portion 10c having flexibility. A proximal end of the flexible tube portion 10c is continuously connected to a distal end of the operating unit 11. In the distal end portion 10a, a distal end portion of a treatment instrument channel described later is disposed to project a distal end of a treatment instrument.

The operating unit 11 includes the bending knob 11a. Furthermore, the operating unit 11 is provided with a treatment instrument insertion opening 11b introducing, into the subject, a puncture needle or the like as the treatment instrument providing medical treatment to the subject. The insertion section 10 is internally provided with a treatment instrument insertion passage described later, and the treatment instrument insertion opening 11b is formed as an insertion opening for the treatment instrument insertion passage.

The ultrasound endoscope 2 and the endoscope observation device 3 are electrically connected by the video cable 7 connected to the connector portion 13. The ultrasound endoscope 2 and the ultrasound observation device 4 are electrically connected by the ultrasound cable 8 connected to the connector portion 13. The light source cable 9 has an optical fiber cable. The ultrasound endoscope 2 and the light source device 6 guide illumination light from the light source of the light source device 6 to the ultrasound endoscope 2 by the light source cable 9 connected to the connector portion 13.

Figure 2:
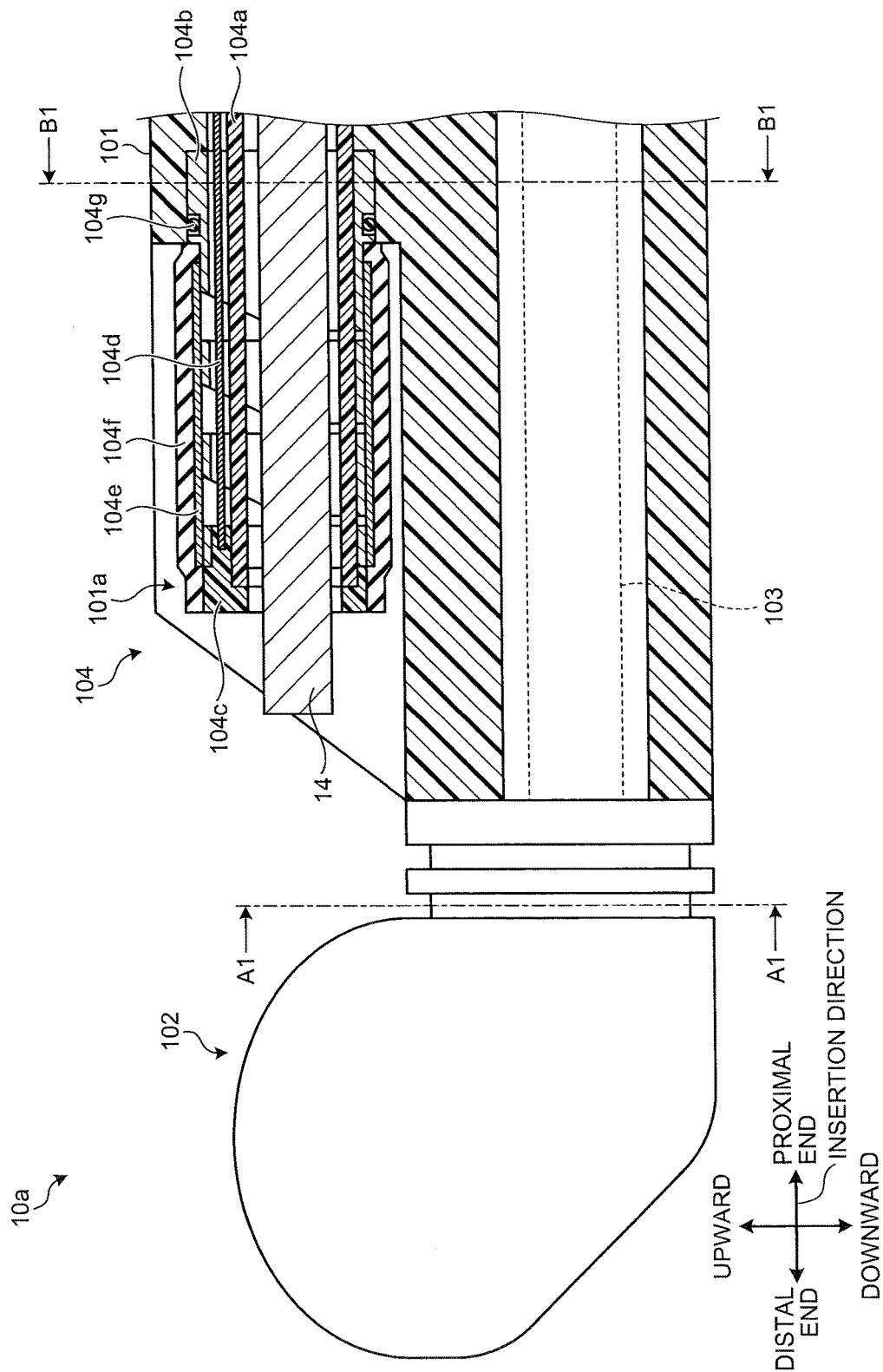
FIG. 2 is a schematic partial cross-sectional view of a distal rigid portion of the ultrasound endoscope illustrated in FIG. 1.

FIG. 2 is a schematic partial cross-sectional view of a distal rigid portion of the ultrasound endoscope illustrated in FIG. 1. The distal end portion 10a includes a distal rigid portion 101 positioned near the distal end of the insertion section 10, an ultrasound transducer unit 102 disposed at a distal end of the distal rigid portion 101, and a signal cable 103 connected to a proximal end of the ultrasound transducer unit 102.

Figure 3:
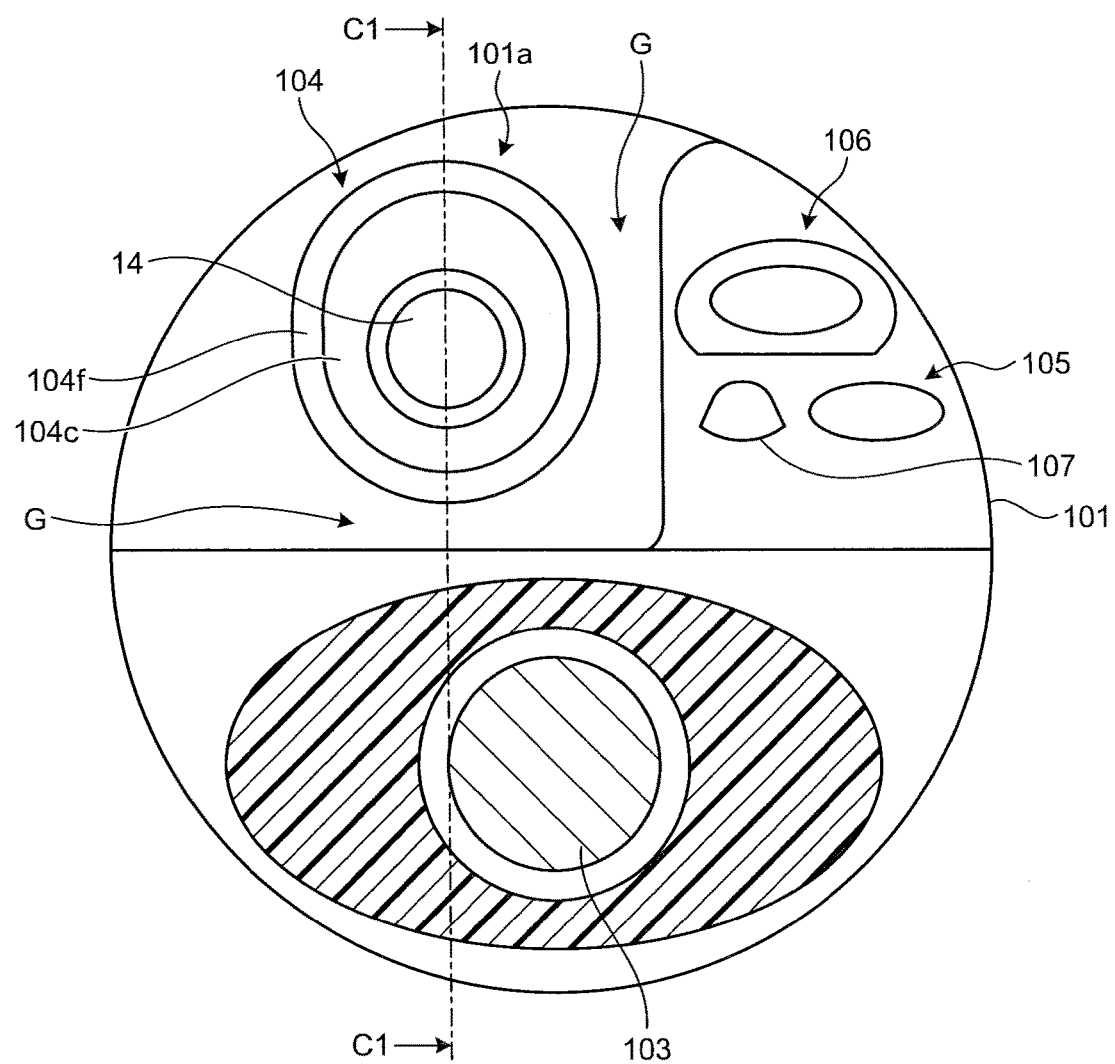
FIG. 3 is a cross-sectional view taken along the line A1-A1 of FIG. 2.
Figure 4:
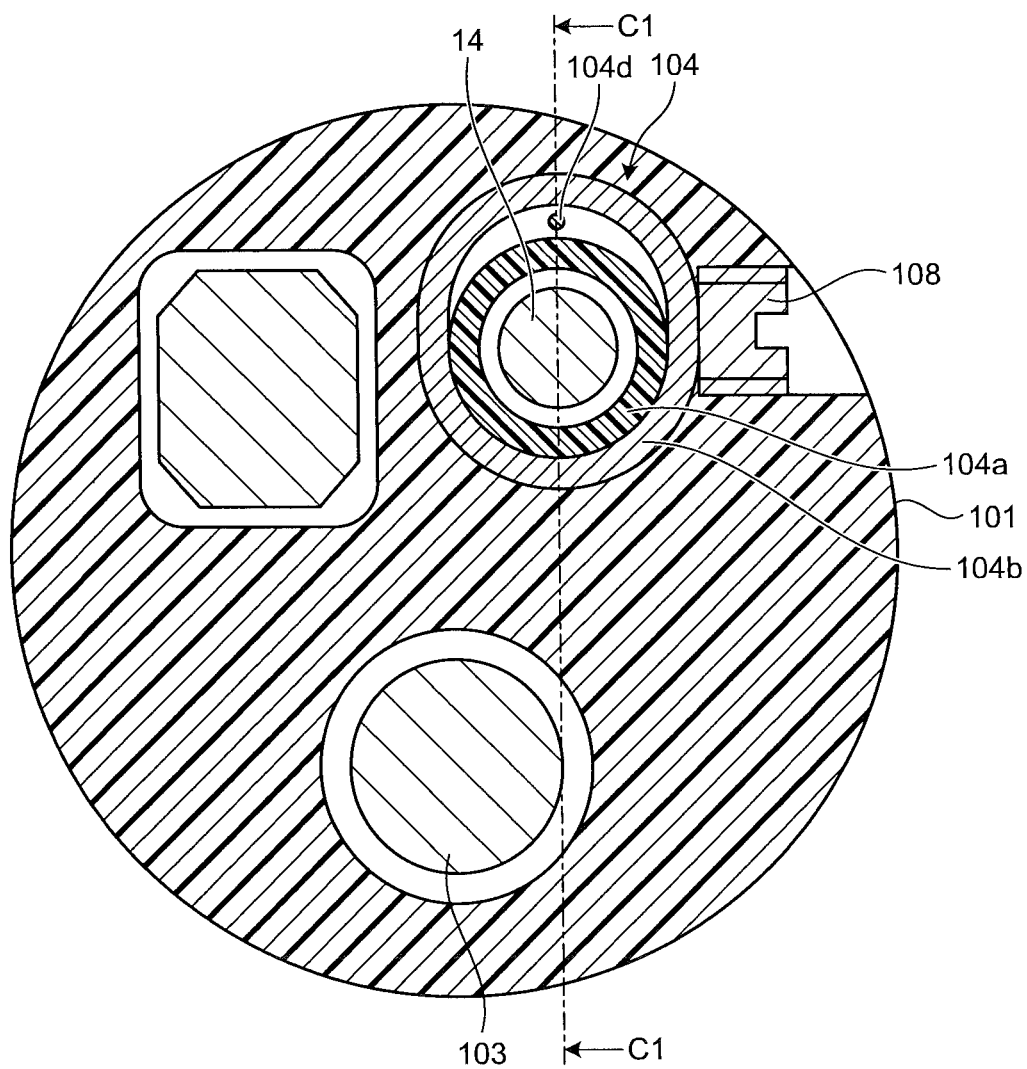
FIG. 4 is a cross-sectional view taken along the line B1-B1 of FIG. 2.

FIG. 3 is a cross-sectional view taken along the line A1-A1 of FIG. 2. As illustrated in FIGS. 2 and 3, the distal end portion 10a includes the distal end portion of a treatment instrument channel 104 through which a treatment instrument 14 is inserted, an illumination unit 105, an imaging unit 106, and an air/water opening 107. FIG. 4 is a cross-sectional view taken along the line B1-B1 of FIG. 2. As illustrated in FIG. 4, the distal end portion 10a includes a screw 108. Note that the cross-section of FIG. 2 is a cross-section corresponding to the line C1-C1 of FIGS. 3 and 4. Furthermore, in the present description, "upward" represents an upper side of a drawing of each figure, as illustrated in FIG. 2, and "downward" represents a lower side of a drawing of each figure, as illustrated in FIG. 2, in the following description.

The distal rigid portion 101 includes a rigid member made of a metal, a rigid resin, or the like. The distal rigid portion 101 includes an aperture portion 101a formed to store the distal end portion of the treatment instrument channel 104.

The ultrasound transducer unit 102 includes an ultrasound transducer transmitting an ultrasound wave, and receiving an ultrasound wave (ultrasound echo) reflected from the object to be observed. An observation direction of the ultrasound transducer unit 102 is within a predetermined range of a lateral side (upper side in the drawing of FIG. 2) of the insertion section 10. This observation direction of the ultrasound transducer unit 102 may be changed by bending movement of the bending section 10b. Furthermore, the signal cable 103 is connected to the ultrasound transducer unit 102, and the signal cable 103 is electrically connected to the ultrasound observation device 4 through the universal cord 12 and the ultrasound cable 8.

The treatment instrument channel 104 has a tubular shape, and projects the treatment instrument 14 inserted from the treatment instrument insertion opening 11b of the operating unit 11 from the distal end portion 10a of the insertion section 10. As seen from FIG. 3, in a cross-section orthogonal to the insertion direction, the treatment instrument channel 104 in an initial state before raising the treatment instrument 14 described later is preferably stored in the aperture portion 101a. That is because when the treatment instrument channel 104 has a projecting portion from the aperture portion 101a, the projecting portion of the treatment instrument channel 104 may inhibit insertion of the insertion section 10 to insert the insertion section 10 into the subject. Furthermore, as seen from FIG. 3, a gap G is provided between the distal rigid portion 101 and the treatment instrument channel 104. The gap G is preferably for example not less than 0.1 mm and not more than 3 mm.

The illumination unit 105 emits illumination light from the light source device 6 to the object to be observed (surface of organ or the like). The imaging unit 106 includes the optical system focusing light reflected from a surface of the object to be observed, such as an organ, and the imaging element performing O/E conversion on the focused light and outputting an electrical signal. An observation direction of the imaging unit 106 extends obliquely to the insertion section 10 (upper left side in the drawing of FIG. 2). This observation direction of the imaging unit 106 may be changed by bending movement of the bending section 10b.

The air/water opening 107 supplies air or water into the subject. As illustrated in FIG. 4, the screw 108 is threadedly engaged with a screw hole of the distal rigid portion 101 to fix the treatment instrument channel 104 in the distal rigid portion 101. Furthermore, the screw hole is sealed with an adhesive or the like to maintain water tightness.

Next, a configuration of the distal end portion of the treatment instrument channel 104 will be described in detail. As illustrated in FIG. 2, the distal end portion of the treatment instrument channel 104 includes a treatment instrument insertion passage 104a communicating with the treatment instrument insertion opening 11b of the operating unit 11, a distal bending portion 104b disposed on an outer periphery of a distal end of the treatment instrument insertion passage 104a, a distal end member 104c disposed at the distal end of the treatment instrument insertion passage 104a, a wire 104d disposed along the insertion direction and connected to the distal end member 104c, a bending rubber 104f as a coating portion covering the distal bending portion 104b and the wire 104d through a braid 104e, and an O-ring 104g sealing between the distal rigid portion 101 and the distal bending portion 104b.

The treatment instrument insertion passage 104a has a tubular member made of resin or the like and having flexibility. The treatment instrument insertion passage 104a allows insertion of the treatment instrument 14 inserted from the treatment instrument insertion opening 11b of the operating unit 11, and projection of the treatment instrument 14 from the aperture portion of the distal rigid portion 101.

Figure 5:
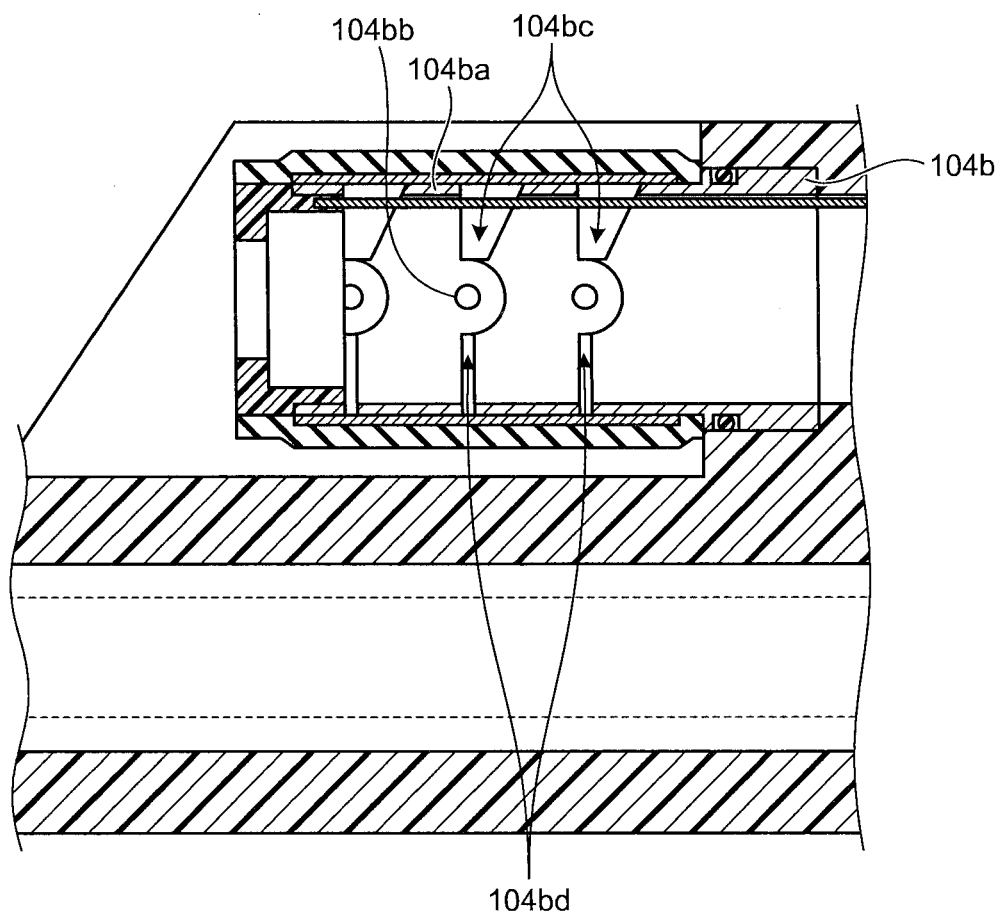
FIG. 5 is a diagram illustrating a structure of a distal bending portion of FIG. 2.

FIG. 5 is a diagram illustrating a structure of the distal bending portion of FIG. 2. Furthermore, in FIG. 5, the treatment instrument 14 and the treatment instrument insertion passage 104a of FIG. 2 are removed. The configuration of the distal bending portion 104b will be described in detail with reference to FIGS. 2 and 5. The distal bending portion 104b includes an articulated ring structure in which ring-shaped members 104ba are riveted with pins 104bb to be turnably connected. Each of the ring-shaped members 104ba has a width located above the corresponding pin 104bb, and decreasing upward. Therefore, the distal bending portion 104b has gaps 104bc each formed to have a width decreasing downward. In contrast, the ring-shaped member 104ba has a constant width below the pin 104bb. Therefore, the distal bending portion 104b has gaps 104bd each formed to have a constant width. Furthermore, the ring-shaped members 104ba contains the treatment instrument insertion passage 104a having a circular cross-section in the cross-section of FIG. 4 (cross-section orthogonal to the insertion direction), and the wire 104d disposed only above the treatment instrument insertion passage 104a. Thus, the ring-shaped members 104ba have an oval cross-section having a major axis in a vertical direction of the cross-section. The ring-shaped member 104ba and the pin 104bb are for example members including a metal such as stainless steel.

The distal end member 104c is an annular member including for example a resin or a metal, and is bonded to the treatment instrument insertion passage 104a.

The wire 104d has one end fixed to the distal end member 104c with an adhesive, by brazing, or the like, and the other end connected to an operation unit such as a lever of the operating unit 11. The wire 104d may be moved along the insertion direction, according to raising operation from the operation unit by a user, such as a physician.

The braid 104e is a metal braided cylindrical member, and is disposed on an outer periphery of the distal bending portion 104b. During raising movement of the distal end portion of the treatment instrument channel 104 described later, the braid 104e prevents the bending rubber 104f from being caught for example between the ring-shaped members 104ba of the distal bending portion 104b.

The bending rubber 104f is provided to cover the outer periphery of the distal bending portion 104b, and has a proximal end bonded to a proximal end portion of the distal bending portion 104b, and a distal end bonded to the distal end member 104c. Thus, the bending rubber 104f covers the distal bending portion 104b and the wire 104d, and water tightness of the distal bending portion 104b and the wire 104d are maintained.

The O-ring 104g includes an elastic member of silicon or the like, is fitted into a groove formed in the proximal end portion of the distal bending portion 104b, and seals between the distal rigid portion 101 and the distal bending portion 104b to ensure water tightness.

Next, movement of the distal end portion of the treatment instrument channel 104 will be described. First, in an initial state of FIG. 2, when the operation unit of the operating unit 11 performs the raising operation to pull the wire 104d to the proximal end, the distal end member 104c and the upper portions of the ring-shaped members 104ba of the distal bending portion 104b are moved toward the proximal end, in association with the wire 104d. Then, each of the ring-shaped members 104ba of the distal bending portion 104b turns around the pins 104bb.

Figure 6:
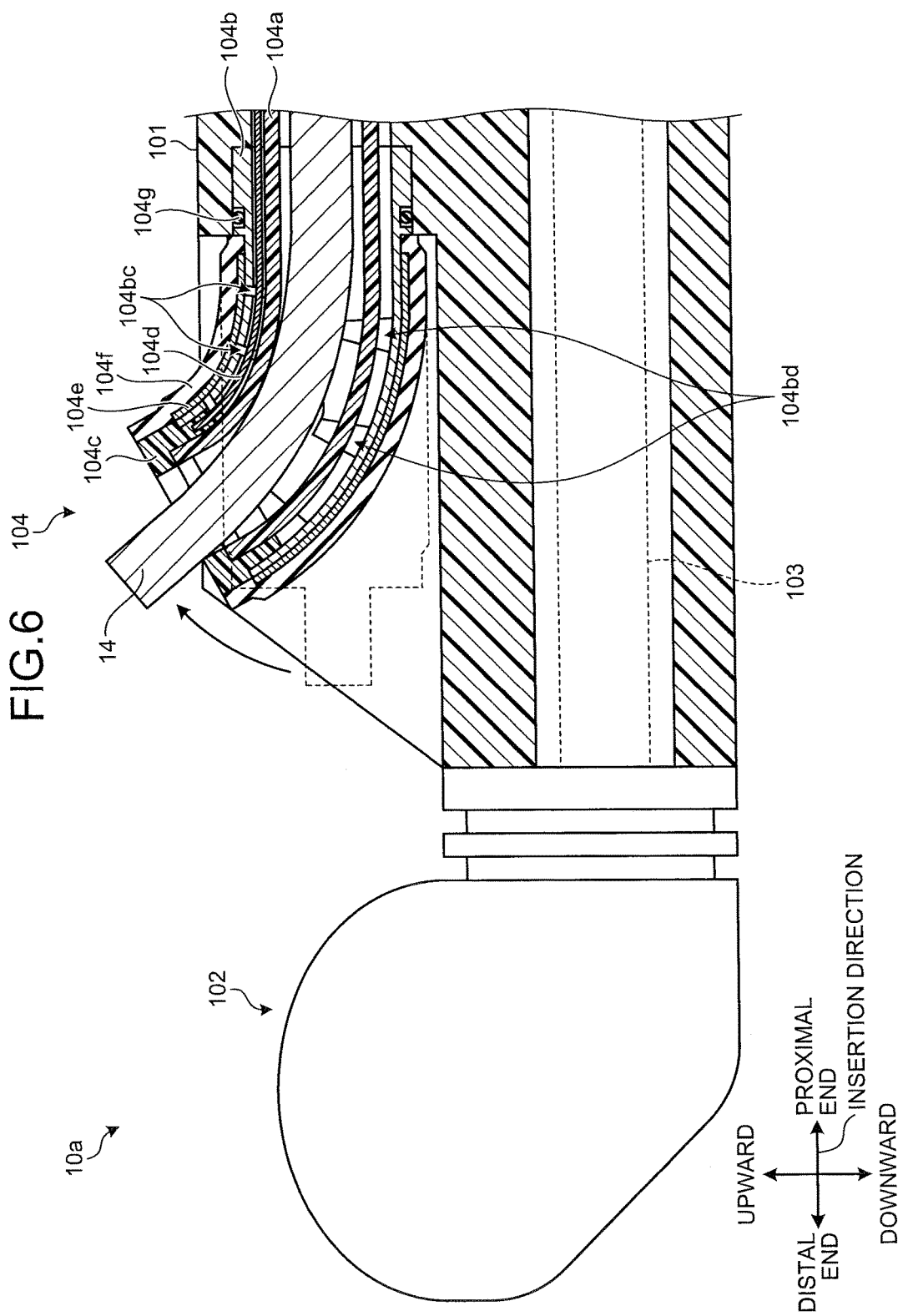
FIG. 6 is a schematic partial cross-sectional view illustrating a state in which a distal end portion of a treatment instrument channel of FIG. 2 raises a treatment instrument.

FIG. 6 is a schematic partial cross-sectional view illustrating a state in which the distal end portion of the treatment instrument channel of FIG. 2 raises the treatment instrument. In FIG. 6, a broken line represents the initial state of the distal end portion of the treatment instrument channel 104. As illustrated in FIG. 6, when the ring-shaped members 104ba of the distal bending portion 104b are turned, the width of the gaps 104bc on the upper side of the distal bending portion 104b is reduced, the width of the gaps 104bd on the lower side of the distal bending portion 104b is increased, and the distal bending portion 104b is bent upward. Then, the treatment instrument insertion passage 104a, the bending rubber 104f, and the like having flexibility are bent together with and in association with the distal bending portion 104b, and the distal end portion of the treatment instrument channel 104 is bent as a whole. Then, in association with the movement of the distal end portion of the treatment instrument channel 104, the treatment instrument 14 inserted through the treatment instrument channel 104 is raised. In this configuration, the observation directions of the imaging unit 106 and the ultrasound transducer unit 102 are maintained. Accordingly, the ultrasound endoscope 2 may independently change a direction (projecting direction) in which the treatment instrument 14 projects from the treatment instrument channel 104, and the observation directions of the imaging unit 106 and the ultrasound transducer unit 102.

Here, in the ultrasound endoscope 2, a movable portion is coated for water-tightness by the bending rubber 104f. The movable portion has a complicated configuration such as the distal bending portion 104b and the wire 104d having a function for raising the treatment instrument 14. That is, the distal end portion of the treatment instrument channel 104 is coated for water tightness, and has a bendable configuration. Accordingly, in the ultrasound endoscope 2, a portion having no water tightness and required to be cleaned has no complicated configuration, and the ultrasound endoscope 2 has improved cleaning efficiency. Accordingly, the ultrasound endoscope 2 according to the present first embodiment is an endoscope having improved cleaning efficiency.

Furthermore, in the ultrasound endoscope 2, as illustrated in FIG. 3, the gap G is provided between the distal rigid portion 101 and the treatment instrument channel 104, so that a portion around the distal end portion of the treatment instrument channel 104 may be directly cleaned with a brush for improved cleaning efficiency. Note that the gap G preferably has a sufficient width to receive at least bristles of the brush inserted, from the viewpoint of cleaning efficiency. Meanwhile the width of the gap G is preferably not so large, from the viewpoint of reduction in size of the distal end portion 10a. In order to meet these demands, the gap G is not less than 0.1 mm and not more than 3 mm.

Furthermore, the treatment instrument channel 104 of the ultrasound endoscope 2 according to the first embodiment includes a single wire 104d only above the distal bending portion 104b. Thus, as illustrated in FIG. 4, the distal bending portion 104b has the oval cross-section to have a reduced diameter, in comparison with a structure having a plurality of wires described later, and has an advantageous configuration for reduction in size of the distal end portion 10a. Note that the wire 104d may be formed only below the distal bending portion 104b. Furthermore, a treatment instrument raiser of a conventional endoscope is configured to have a single wire for raising movement, and for example has an operation lever, as an operation unit for raising operation of this wire. In the ultrasound endoscope 2, the raising operation of the distal end portion of the treatment instrument channel 104 is performed using the single wire 104d, and thus the operation lever of the conventional configuration may be directly used.

Figure 7:
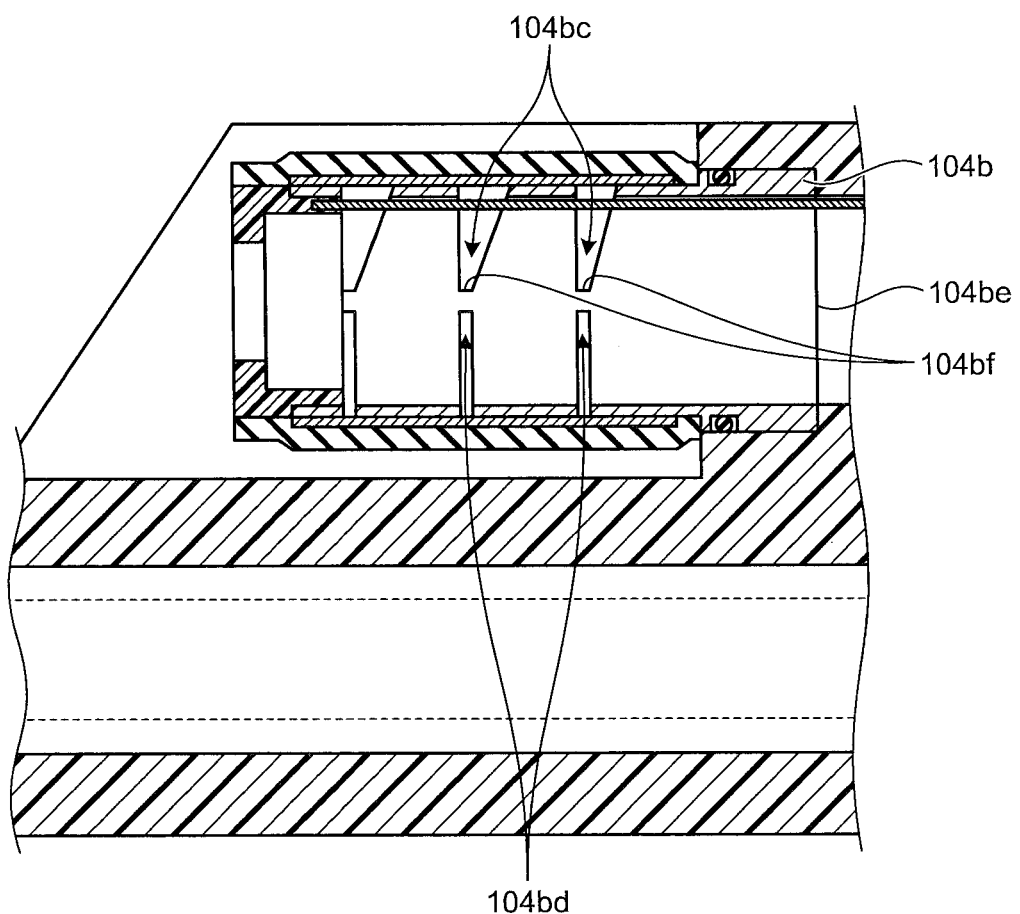
FIG. 7 is a diagram illustrating another structure of the distal bending portion of FIG. 2.

Furthermore, the configuration of the distal bending portion 104b is not limited to the articulated ring structure illustrated in FIG. 5. FIG. 7 is a diagram illustrating another structure of the distal bending portion of FIG. 2. In FIG. 7, as in FIG. 5, the treatment instrument 14 and the treatment instrument insertion passage 104a of FIG. 2 are removed. This distal bending portion 104b includes for example a tubular member 104be having a tube including a super elastic alloy. Then, in the tubular member 104be, the gaps 104bc and the gaps 104bd are formed as a slit for reducing power required for the bending operation input to the operating unit 11. Furthermore, the distal bending portion 104b includes a single member having connection portions 104bf.

Each of the gaps 104bc is located above the corresponding connection portion 104bf, and has a width reduced downward, and each of the gaps 104bd is located below the corresponding connection portion 104bf, and has a constant width. In this configuration, when the wire 104d is pulled toward the proximal end, the tubular member 104be is bent around the connection portions 104bf, the width of the gaps 104bc on the upper side of the tubular member 104be is reduced, and the width of the gaps 104bd on the lower side of the tubular member 104be is increased, and the distal bending portion 104b is bent upward. The distal bending portion 104b having such a configuration may be used for raising movement. Note that, in this configuration, the distal bending portion 104b may be constituted by one member, so that the manufacturing process may be simplified to reduce manufacturing cost.

Second Embodiment

Figure 8:
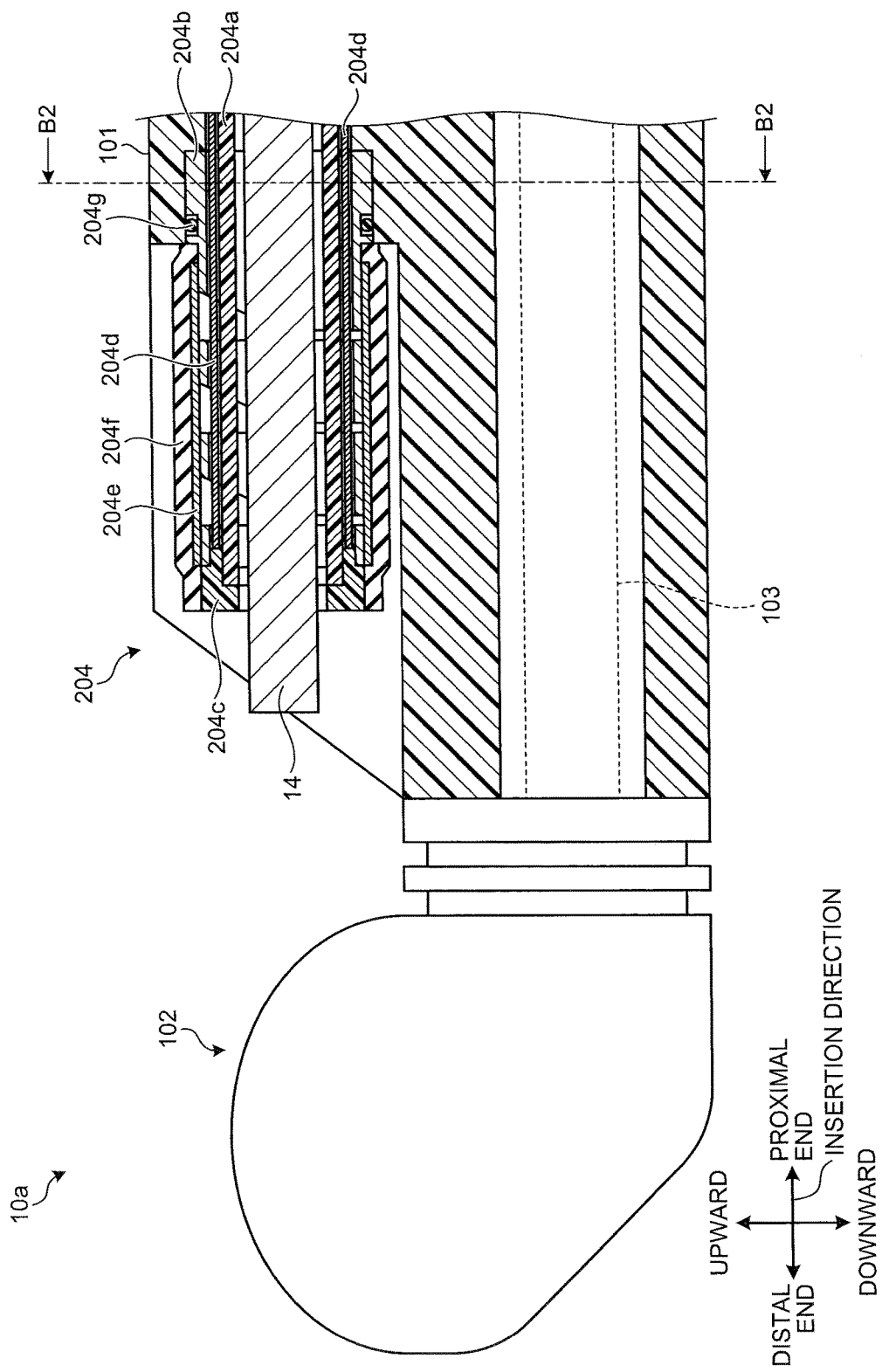
FIG. 8 is a schematic view illustrating a configuration of a main portion of an ultrasound diagnostic system which includes an ultrasound endoscope according to a second embodiment of the present disclosure.

Next, a second embodiment of the present disclosure will be described. FIG. 8 is a schematic view illustrating a configuration of a main portion of an ultrasound diagnostic system which includes an ultrasound endoscope according to a second embodiment of the present disclosure. Except for a configuration of a distal end portion of a treatment instrument channel 204, the ultrasound endoscope according to the second embodiment has the same configuration as that of the ultrasound endoscope 2 according to the first embodiment, and description of the same configuration will be omitted appropriately.

The distal end portion of the treatment instrument channel 204 includes a treatment instrument insertion passage 204a communicating with the treatment instrument insertion opening 11b of the operating unit 11, a distal bending portion 204b disposed on an outer periphery of the distal end of the treatment instrument insertion passage 204a, a distal end member 204c disposed at a distal end in an insertion direction of the treatment instrument insertion passage 204a, a wire 204d disposed along the insertion direction and connected to the distal end member 204c, a bending rubber 204f as a coating portion covering the distal bending portion 204b and the wire 204d for water tightness through a braid 204e, and an O-ring 204g sealing between the distal rigid portion 101 and the distal bending portion 204b to ensure water tightness.

Figure 9:
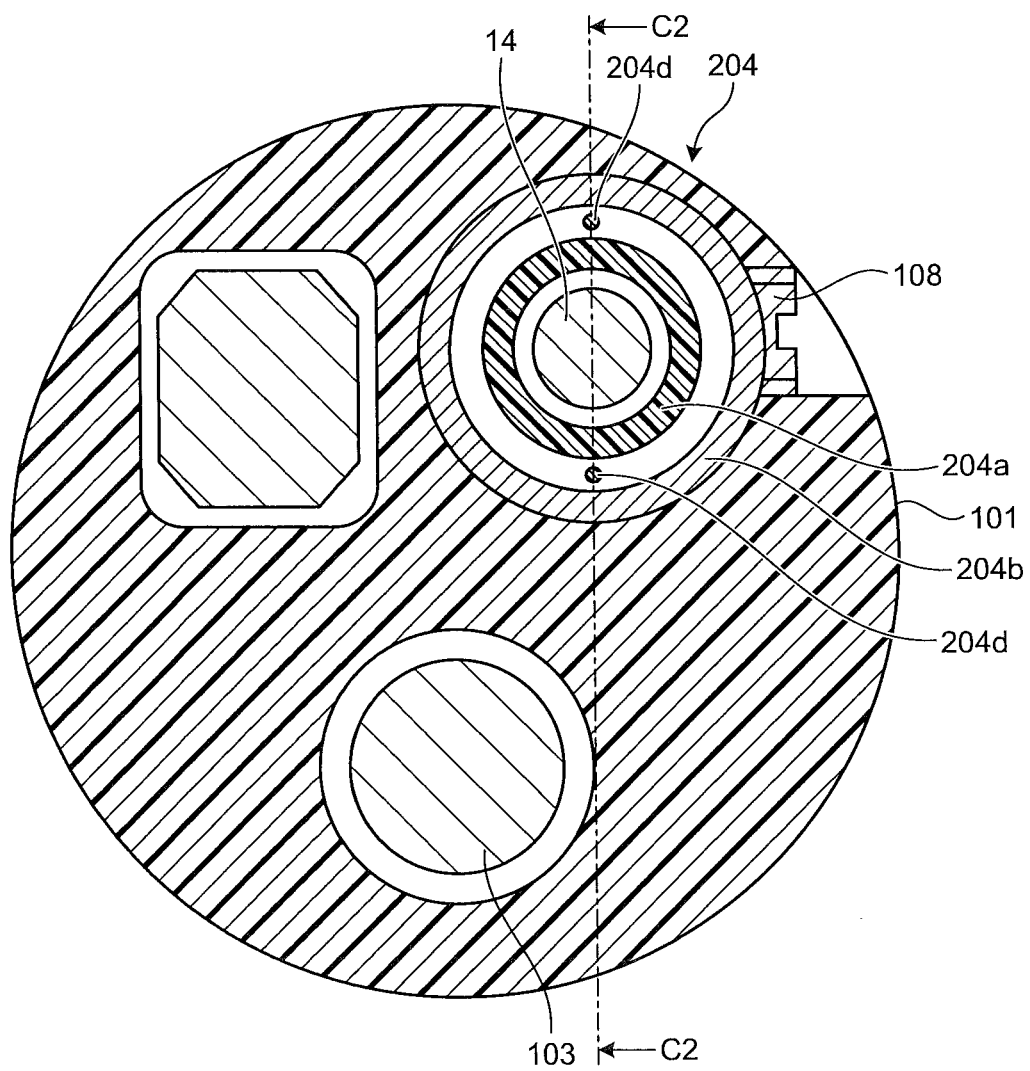
FIG. 9 is a cross-sectional view taken along the line B2-B2 of FIG. 8.

FIG. 9 is a cross-sectional view taken along the line B2-B2 of FIG. 8. The cross-section of FIG. 8 is a cross-section corresponding to the line C2-C2 of FIG. 9. As illustrated in FIG. 9, the wire 204d includes two wires respectively disposed above and below the distal bending portion 204b. Then, when the distal end portion of the treatment instrument channel 204 is raised, an upper wire 204d is pulled toward the proximal end, and a lower wire 204d is pressed toward the distal end in cooperation with pulling of the upper wire 204d. Thus, the treatment instrument channel 204 according to the second embodiment is moved smoother than the treatment instrument channel 104 of the ultrasound endoscope 2 according to the first embodiment having the single wire. Accordingly, the ultrasound endoscope according to the second embodiment may independently change a direction (projecting direction) in which the treatment instrument 14 projects from the treatment instrument channel 204, and the observation directions of the imaging unit 106 and the ultrasound transducer unit 102.

Note that, in order to fall the raised treatment instrument channel 204 to the initial state, it is only required to pull the lower wire 204d toward the proximal end, and press the upper wire 204d toward the distal end in cooperation with pulling of the upper wire 204d. Here, the wire 204d is more suitable for transmission of pulling operation than for transmission of pressing operation, and, in particular, the ultrasound endoscope according to the second embodiment may provide smoother falling operation than an ultrasound endoscope having one wire.

Furthermore, the upper wire 204d and the lower wire 204d may have configurations cooperating with each other, but may have configurations for independent movement.

Here, in the ultrasound endoscope according to the second embodiment, the distal bending portion 204b, the wires 204d, and the like having a function of raising the treatment instrument 14 are coated for water tightness by the bending rubber 204f. That is, the distal end portion of the treatment instrument channel 204 is coated for water tightness, and has a bendable configuration. Accordingly, in the ultrasound endoscope according to the second embodiment, a portion having no water tightness and required to be cleaned has no complicated configuration, and the ultrasound endoscope has improved cleaning efficiency. Accordingly, the ultrasound endoscope according to the present second embodiment is an endoscope having improved cleaning efficiency.

Third Embodiment

Figure 10:
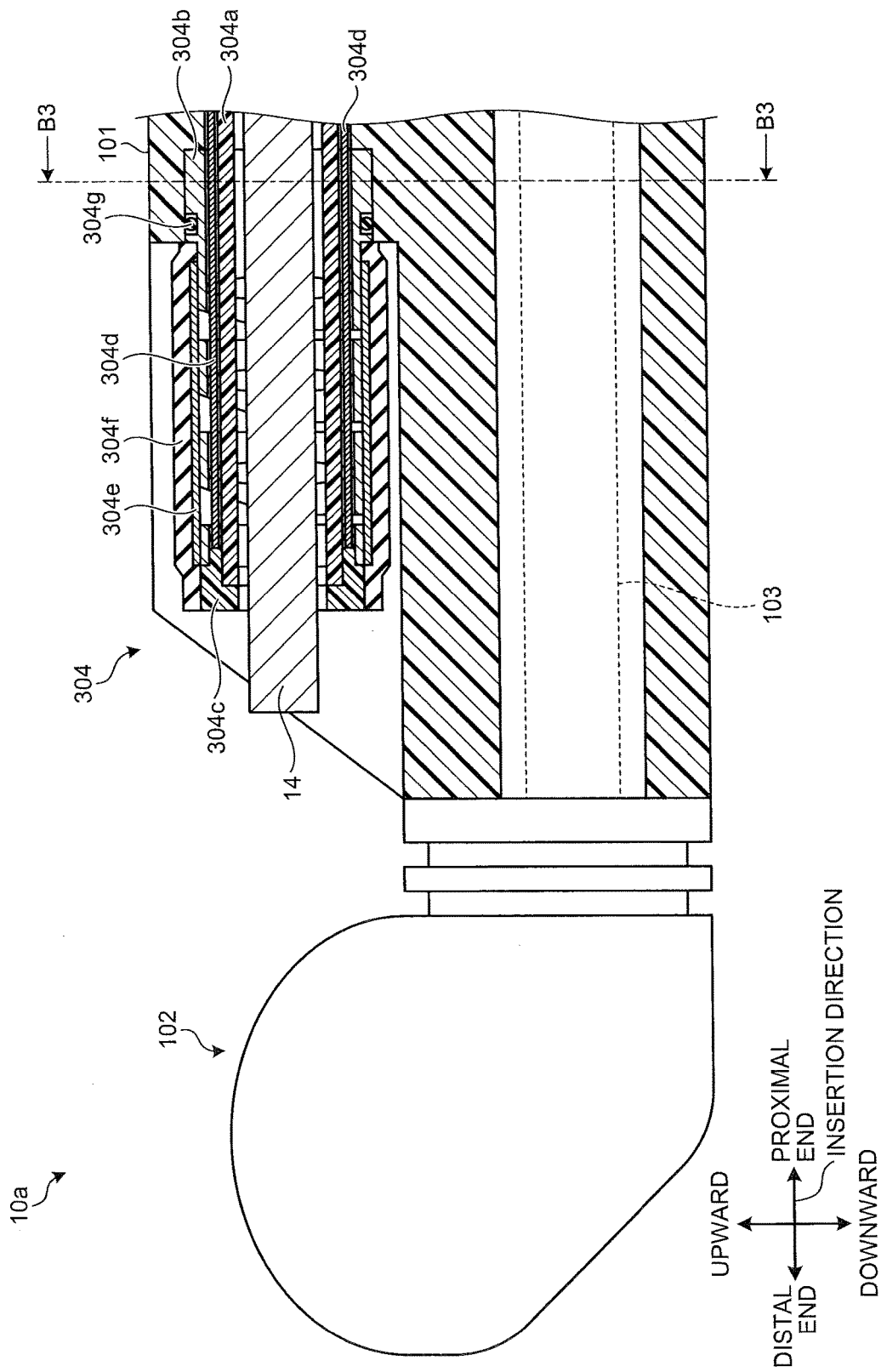
FIG. 10 is a schematic view illustrating a configuration of a main portion of an ultrasound diagnostic system which includes an ultrasound endoscope according to a third embodiment of the present disclosure.

Next, a third embodiment of the present disclosure will be described. FIG. 10 is a schematic view illustrating a configuration of a main portion of an ultrasound diagnostic system which includes an ultrasound endoscope according to a third embodiment of the present disclosure. Except for a configuration of a distal end portion of a treatment instrument channel 304, the ultrasound endoscope according to the third embodiment has the same configuration as that of the ultrasound endoscope 2 according to the first embodiment, and description of the same configuration will be omitted appropriately.

The distal end portion of the treatment instrument channel 304 includes a treatment instrument insertion passage 304a communicating with the treatment instrument insertion opening 11b of the operating unit 11, a distal bending portion 304b disposed on an outer periphery of the distal end of the treatment instrument insertion passage 304a, a distal end member 304c disposed at a distal end in an insertion direction of the treatment instrument insertion passage 304a, a wire 304d disposed along the insertion direction and connected to the distal end member 304c, a bending rubber 304f as a coating portion covering the distal bending portion 304b and the wire 304d for water tightness through a braid 304e, and an O-ring 304g sealing between the distal rigid portion 101 and the distal bending portion 304b to ensure water tightness.

Figure 11:
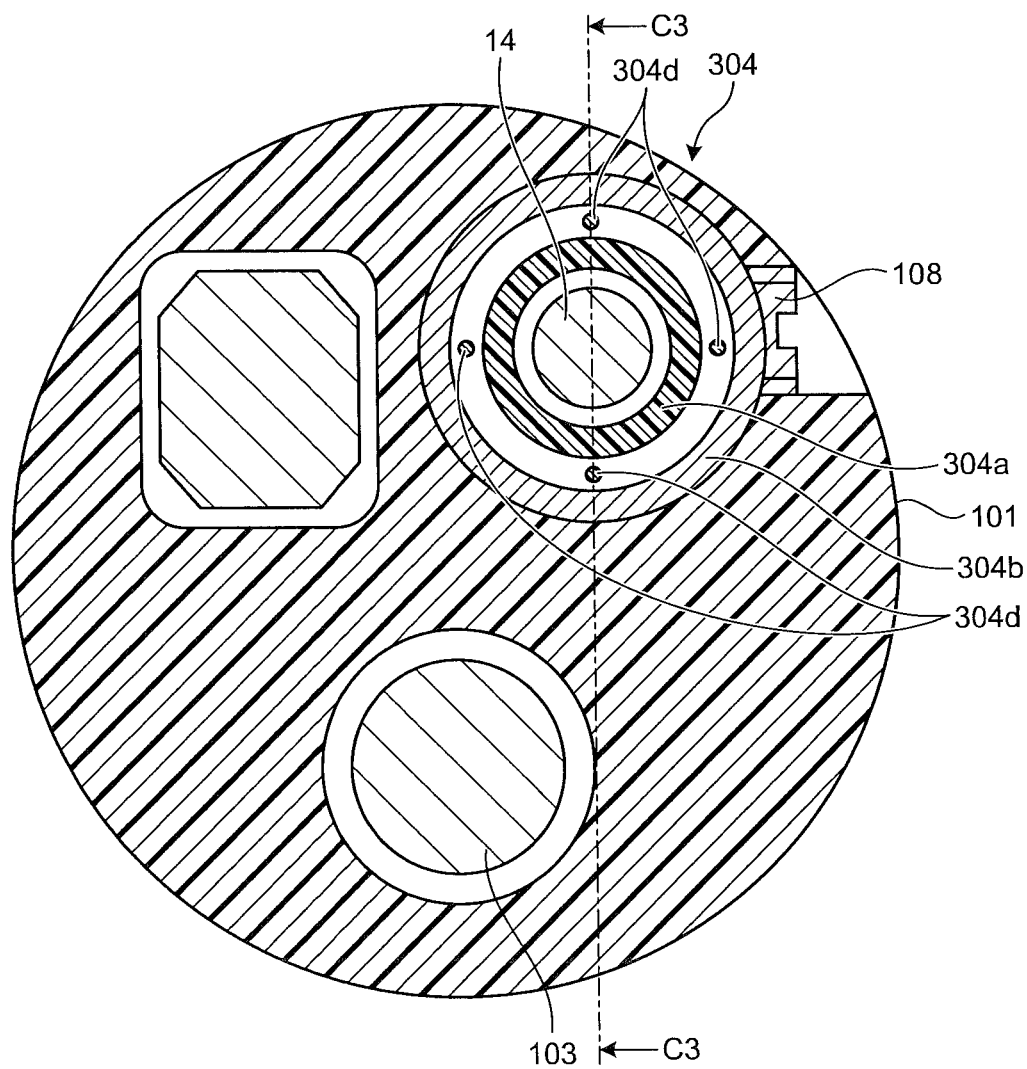
FIG. 11 is a cross-sectional view taken along the line B3-B3 of FIG. 10.

FIG. 11 is a cross-sectional view taken along the line B3-B3 of FIG. 10. The cross-section of FIG. 10 is a cross-section corresponding to the line C3-C3 of FIG. 11. As illustrated in FIG. 11, the wire 304d includes four wires respectively disposed above and below, and to the right and left of the distal bending portion 304b.

Figure 12:
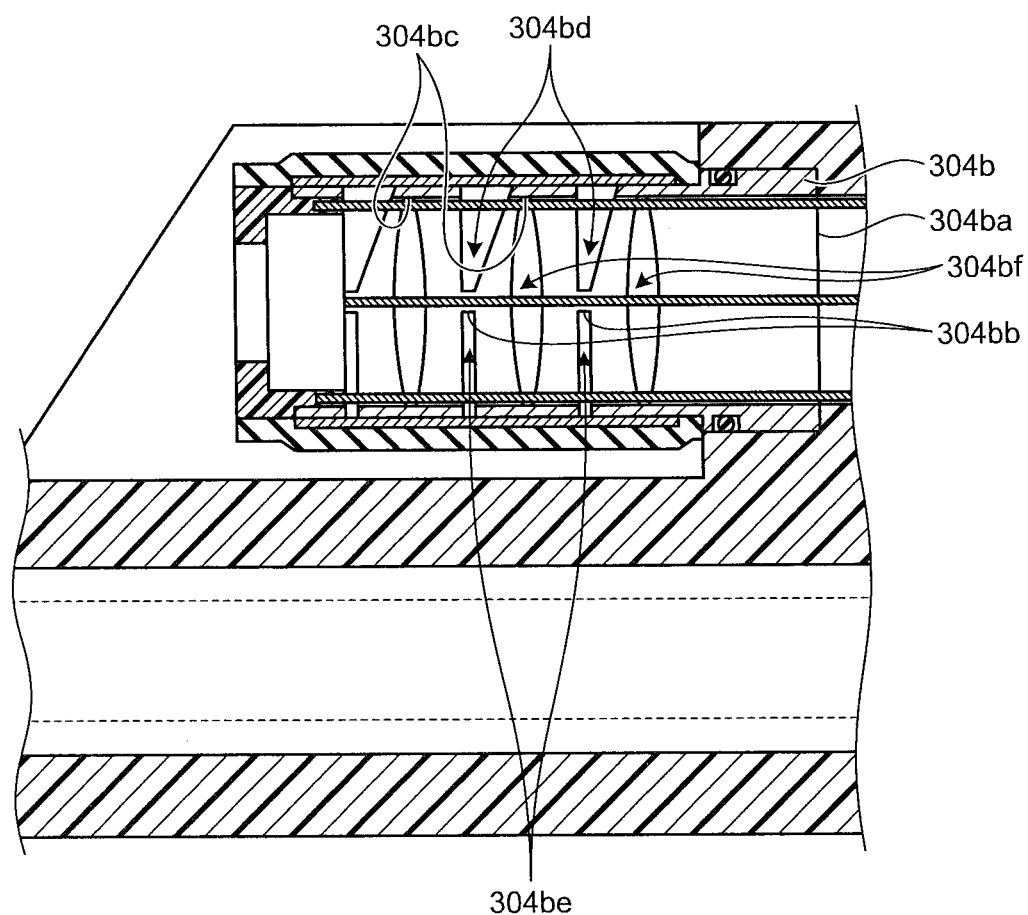
FIG. 12 is a diagram illustrating a structure of a distal bending portion of FIG. 10.

FIG. 12 is a diagram illustrating a structure of the distal bending portion of FIG. 10. In FIG. 12, the treatment instrument 14 and the treatment instrument insertion passage 304a of FIG. 10 are removed. The distal bending portion 304b includes a tubular member 304ba having an integrated configuration having connection portions 304bb in a horizontal direction (back and forth direction in the drawing of FIG. 12), and connection portions 304bc in a vertical direction. Then, the tubular member 304ba has gaps 304bd each positioned above the corresponding connection portion 304bb and having a width decreasing downward, and gaps 304be each located below the corresponding connection portion 304bb and having a constant width. Furthermore, the tubular member 304ba has gaps 304bf each having a width decreasing toward the corresponding connection portion 304bc. Owing to this configuration, the distal end portion of the treatment instrument channel 304 allows raising movement of the treatment instrument 14 using the wires 304d vertically located, and horizontal movement of the treatment instrument 14 using the wires 304d horizontally located. Accordingly, the ultrasound endoscope according to the present third embodiment may change the projecting direction of the treatment instrument 14, independently of the observation direction of the endoscope. Then, the ultrasound endoscope according to the present third embodiment has a function unavailable from a conventional treatment instrument raiser, for example, a function for adjusting a horizontal position of the treatment instrument 14 upon puncture of a puncture needle inserted into the treatment instrument channel 304 to a region of interest of a subject.

Here, in the ultrasound endoscope according to the third embodiment, the distal bending portion 304b, the wires 304d, and the like having a function of raising the treatment instrument 14 are coated for water tightness by the bending rubber 304f. That is, the distal end portion of the treatment instrument channel 304 is coated for water tightness, and has a bendable configuration. Accordingly, in the ultrasound endoscope according to the third embodiment, a portion having no water tightness and required to be cleaned has no complicated configuration, and the ultrasound endoscope has improved cleaning efficiency. Accordingly, the ultrasound endoscope according to the present third embodiment is an endoscope having improved cleaning efficiency.

Note that as long as the distal bending portion according to the present disclosure has a bendable structure, the structure of the distal bending portion is not particularly limited. For example, also in the ultrasound endoscope according to the third embodiment, such an articulated ring structure as illustrated in FIG. 5 may be used for the distal bending portion 304b.

Furthermore, in the embodiments described above, the one wire (first embodiment), two wires (second embodiment), and four wires (third embodiment) have been exemplified, but the number of wires is not particularly limited.

Furthermore, in the embodiments described above, the endoscope employs, for description, an oblique-viewing endoscope in which the imaging unit has an oblique observation direction, but the endoscope is not limited to the oblique-viewing endoscope. For example, a forward-viewing endoscope performing observation in a direction along an insertion direction, or a side-viewing endoscope performing observation in a direction orthogonal to an insertion direction may be employed. In the case of the forward-viewing endoscope or the side-viewing endoscope, the configurations according to the embodiments described above may be also applied to change the projecting direction of the treatment instrument 14, independently of the observation direction of the endoscope.

The present disclosure provides an endoscope which has improved cleaning efficiency.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion section configured to be inserted into a subject;
   an operating unit continuously connected to a proximal end of the insertion section;
   an observation unit disposed at a distal end of the insertion section, the observation unit being configured to observe the subject;
   a treatment instrument insertion passage configured to allow insertion of a treatment instrument providing medical treatment to the subject, the treatment instrument insertion passage being further configured to project the treatment instrument from a distal end portion of the insertion section;

a distal bending portion disposed at a distal end of the treatment instrument insertion passage, the distal bending portion being configured to bend according to a raising operation of the operating unit, the distal bending portion including a tube including a super elastic alloy and a slit formed to reduce power required for the bending operation, the distal bending portion being configured to raise the treatment instrument;

a wire provided to pass through a space between the treatment instrument insertion passage and the distal bending portion, the wire being configured to cause the distal bending portion to bend according to the raising operation of the operating unit; and a bending rubber provided to cover the distal bending portion.

2. The endoscope according to claim 1, wherein the distal bending portion changes, according to the raising operation of the operating unit, a direction in which the treatment instrument projects, independently of a direction in which the observation unit performs observation.

3. The endoscope according to claim 1, wherein
the wire is disposed along a direction in which the insertion section extends, and is connected to the operating unit, and
the wire includes a distal end portion covered by the bending rubber.

4. The endoscope according to claim 1, wherein the wire comprises two wires disposed along a direction in which the insertion section extends.

5. The endoscope according to claim 1, wherein the wire comprises four wires disposed along a direction in which the insertion section extends.

6. The endoscope according to claim 1, further comprising
a distal rigid portion disposed near a distal end of the insertion section, the distal rigid portion being formed with an aperture,
wherein, in a cross-section orthogonal to a direction in which the insertion section extends, the distal bending portion in an initial state before the bending is stored in the aperture.

7. The endoscope according to any one of claim 1, wherein
the observation unit includes one of:
an imaging unit including an optical system focusing light reflected from an object to be observed, and an imaging sensor configured to convert the focused light to an electrical signal, and to output the electrical signal, or
an ultrasound transducer unit receiving an ultrasound wave reflected from an object to be observed to output an electrical signal.

8. The endoscope according to claim 1, further comprising a distal end member provided at a distal end of the treatment instrument insertion passage, wherein
the bending rubber is connected to the distal end member so as to provide a water-tight seal between the distal bending portion and the wire.

9. The endoscope according to claim 1, further comprising a seal provided at a proximal end of the distal bending portion so as to provide a water-tight seal between the proximal end of the distal bending portion and a distal rigid portion provided at a proximal end of the insertion section.

10. The endoscope according to claim 1, further comprising a braided metal sleeve provided around the distal bending portion.

11. An endoscope comprising:
an insertion section configured to be inserted into a subject;
an operating unit continuously connected to a proximal end of the insertion section;
an observation unit disposed at a distal end of the insertion section, the observation unit being configured to observe the subject;
a treatment instrument insertion passage configured to allow insertion of a treatment instrument providing medical treatment to the subject, the treatment instrument insertion passage being further configured to project the treatment instrument from a distal end portion of the insertion section;
a distal bending portion disposed at a distal end of the treatment instrument insertion passage, the distal bending portion having an oval cross-section orthogonal to a direction in which the insertion section extends, the distal bending portion being configured to bend according to a raising operation of the operating unit and raise the treatment instrument;
a wire provided to pass through a space between the treatment instrument insertion passage and the distal bending portion, the wire being configured to cause the distal bending portion to bend according to the raising operation of the operating unit; and
a bending rubber provided to cover the distal bending portion.

12. The endoscope according to claim 11, wherein the distal bending portion changes, according to the raising operation of the operating unit, a direction in which the treatment instrument projects, independently of a direction in which the observation unit performs observation.

13. The endoscope according to claim 11, wherein
the wire is disposed along a direction in which the insertion section extends, and is connected to the operating unit, and
the wire includes a distal end portion covered by the bending rubber.

14. The endoscope according to claim 11, further comprising
a distal rigid portion disposed near a distal end of the insertion section, the distal rigid portion being formed with an aperture,
wherein, in a cross-section orthogonal to a direction in which the insertion section extends, the distal bending portion in an initial state before the bending is stored in the aperture.

15. The endoscope according to claim 11, wherein
the observation unit includes one of:
an imaging unit including an optical system focusing light reflected from an object to be observed, and an imaging sensor configured to convert the focused light to an electrical signal, and to output the electrical signal, or
an ultrasound transducer unit receiving an ultrasound wave reflected from an object to be observed to output an electrical signal.

16. The endoscope according to claim 11, further comprising a distal end member provided at a distal end of the treatment instrument insertion passage, wherein
the bending rubber is connected to the distal end member so as to provide a water-tight seal between the distal bending portion and the wire.

17. The endoscope according to claim 11, further comprising a seal provided at a proximal end of the distal bending portion so as to provide a water-tight seal between the proximal end of the distal bending portion and a distal rigid portion provided at a proximal end of the insertion section.

18. The endoscope according to claim 11, further comprising a braided metal sleeve provided around the distal bending portion.

* * * * *